(12) United States Patent
Dahlmann et al.

(10) Patent No.: US 7,435,845 B2
(45) Date of Patent: Oct. 14, 2008

(54) CORROSION AND GAS HYDRATE INHIBITORS HAVING IMPROVED WATER SOLUBILITY AND INCREASED BIODEGRADABILITY

(75) Inventors: Uwe Dahlmann, Heidelberg (DE); Michael Feustel, Koengernheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 583 days.

(21) Appl. No.: 10/783,153

(22) Filed: Feb. 20, 2004

(65) Prior Publication Data

US 2005/0101495 A1    May 12, 2005

(30) Foreign Application Priority Data

Feb. 24, 2003   (DE) .............. 103 07 728

(51) Int. Cl.
*C07C 229/02* (2006.01)
*C07C 229/04* (2006.01)
*C07C 69/003* (2006.01)
*C07C 69/007* (2006.01)
*C07C 23/16* (2006.01)
*C10M 101/00* (2006.01)

(52) U.S. Cl. .............. 560/155; 560/179; 562/553; 562/574; 564/152; 564/158; 252/390; 252/401; 252/403; 507/240; 507/241; 507/242; 508/255; 585/15

(58) Field of Classification Search .............. 252/390, 252/392, 401, 403; 564/152, 158
See application file for complete search history.

(56) References Cited

U.S. PATENT DOCUMENTS

| | | | |
|---|---|---|---|
| 4,730,079 A | 3/1988 | Hofinger et al. | 560/196 |
| 4,997,912 A | 3/1991 | Wirtz et al. | 530/232 |
| 5,135,668 A | 8/1992 | Larsen | 252/8.555 |
| 5,254,138 A | 10/1993 | Kurek | 44/347 |
| 5,460,728 A | 10/1995 | Klomp et al. | 210/698 |
| 5,648,575 A | 7/1997 | Klomp et al. | 585/15 |
| 6,025,302 A | 2/2000 | Pakulski | 507/90 |
| 6,102,986 A | 8/2000 | Klug | 95/153 |
| 6,152,993 A | 11/2000 | Klomp | 95/153 |
| 6,177,497 B1 | 1/2001 | Klug et al. | 524/376 |
| 6,261,346 B1 | 7/2001 | Breuer et al. | 106/14.15 |
| 6,309,663 B1 * | 10/2001 | Patel et al. | 424/450 |
| 6,369,004 B1 | 4/2002 | Klug et al. | 507/90 |
| 6,372,918 B1 | 4/2002 | Feustel et al. | 548/349.1 |
| 6,379,294 B1 | 4/2002 | Buijs et al. | 584/114 |
| 6,452,030 B1 * | 9/2002 | Chosa et al. | 554/52 |
| 7,008,466 B2 | 3/2006 | Collins | 95/153 |
| 7,160,507 B2 * | 1/2007 | Dahlmann et al. | 422/7 |
| 7,183,240 B2 * | 2/2007 | Dahlmann et al. | 507/240 |
| 7,214,814 B2 * | 5/2007 | Dahlmann et al. | 560/155 |
| 7,253,138 B2 * | 8/2007 | Dahlmann et al. | 508/243 |
| 7,341,617 B2 * | 3/2008 | Dahlmann et al. | 95/153 |
| 7,348,451 B2 * | 3/2008 | Dahlmann et al. | 560/155 |
| 2001/0024658 A1 * | 9/2001 | Chen et al. | 424/452 |
| 2002/0107265 A1 * | 8/2002 | Chen et al. | 514/310 |
| 2003/0013614 A1 | 1/2003 | Klug et al. | 507/200 |
| 2004/0030206 A1 | 2/2004 | Dahlmann et al. | 585/15 |
| 2004/0096499 A1 * | 5/2004 | Vaya et al. | 424/468 |
| 2004/0211316 A1 * | 10/2004 | Collins | 95/153 |
| 2007/0221539 A1 * | 9/2007 | Cohrs et al. | 208/18 |

FOREIGN PATENT DOCUMENTS

| | | |
|---|---|---|
| DE | 199 30 683 | 1/2001 |
| DE | 100 59 816 | 4/2002 |
| DE | 101 14 638 | 5/2002 |
| EP | 0 212 265 | 3/1987 |
| EP | 0 320 769 | 6/1989 |
| EP | 0359048 | 3/1990 |
| EP | 0 446 616 | 9/1991 |

(Continued)

OTHER PUBLICATIONS

Abstract for EP 0359 048, Mar. 21, 1990.

(Continued)

*Primary Examiner*—Joseph D Anthony
(74) *Attorney, Agent, or Firm*—Richard P. Silverman

(57) ABSTRACT

Corrosion and gas hydrate inhibitors having improved water solubility and increased biodegradability The invention thus provides the use of compounds of the formula (1)

$$\underset{R^3}{\overset{R^1}{\underset{R^2}{\vphantom{X}}}}\!\!\!\!\!\!\!\!\!N^+\!\!-\!\!B\!\!-\!\!X\!\!-\!\!\overset{O}{\overset{\|}{C}}\!\!-\!\!D\!\!-\!\!\overset{O}{\overset{\|}{C}}\!\!-\!\!Y\!\!-\!\!R^4 \qquad (1)$$

where
  $R^1$, $R^2$ are each independently $C_1$- to $C_{22}$-alkyl, $C_2$- to $C_{22}$-alkenyl, $C_6$- to $C_{30}$-aryl or $C_7$- to $C_{30}$-alkylaryl,
  $R^3$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$,
  $R^4$ is M, hydrogen or an organic radical which optionally contains heteroatoms and has from 1 to 100 carbon atoms,
  B is an optionally substituted $C_1$- to $C_{10}$-alkylene group,
  D is an ethylene group substituted by an organic radical having from 1 to 600 carbon atoms,
  X, Y are each independently O or $NR^6$,
  $R^5$, $R^6$ are each independently hydrogen, $C_1$- to $C_{22}$-alkyl, $C_2$- to $C_{22}$-alkenyl, $C_6$- to $C_{30}$-aryl or $C_7$- to $C_{30}$-alkylaryl, and
  M is a cation
as corrosion and gas hydrate inhibitors, and also the compounds of formula 1.

2 Claims, No Drawings

FOREIGN PATENT DOCUMENTS

| | | |
|---|---|---|
| EP | 0 584 711 | 3/1994 |
| EP | 0 736 130 | 10/1996 |
| EP | 0 824 631 | 2/1998 |
| EP | 0 914 407 | 5/1999 |
| EP | 0 946 788 | 10/1999 |
| WO | WO 98/23792 | 6/1998 |
| WO | WO 99/13197 | 3/1999 |
| WO | WO 00/78706 | 12/2000 |
| WO | WO 01/09082 | 2/2001 |

OTHER PUBLICATIONS

Co-pending U.S. Appl. No. 11/664,861, filed Apr. 5, 2007.

* cited by examiner

CORROSION AND GAS HYDRATE INHIBITORS HAVING IMPROVED WATER SOLUBILITY AND INCREASED BIODEGRADABILITY

The present invention relates to an additive and to a process for corrosion inhibition and gas hydrate inhibition on and in equipment for extracting and transporting hydrocarbons in crude oil extraction and processing.

In industrial processes in which metals come into contact with water or else with biphasic oil-water systems, there is the risk of corrosion. This is particularly marked when the aqueous phase, as in the case of crude oil production and processing operations, has a high salt content or, as a result of dissolved acidic gases such as carbon dioxide or hydrogen sulfide, is acidic. It is therefore not possible to exploit a deposit and to process crude oil without special additives to protect the equipment used.

Although suitable corrosion protectors for crude oil extraction and processing have been known for some time, they will become unacceptable for offshore applications in the future for reasons of environmental protection.

As typical prior art corrosion inhibitors, amides, amido amines and imidazolines of fatty acids and polyamines have extremely good oil solubility and are therefore only present in the corrosive aqueous phase in low concentration as a consequence of poor partitioning equilibria. Accordingly, these products have to be used in high dosage despite their poor biodegradability.

DE-A-199 30 683 describes corresponding amido amines/imidazolines which are obtained by reacting alkylpolyglycol ether carboxylic acids with polyamines and which, as a consequence of better partitioning, can be used in low concentrations.

Quaternary alkylammonium compounds (quats) constitute alternative prior art corrosion protectors which have not only corrosion-inhibiting but also biostatic properties. Despite improved water solubility, the quats, in comparison to the imidazolines for example, exhibit distinctly reduced film persistence and therefore likewise lead to effective corrosion protection only in high dosage. The strong algae toxicity and the moderate biodegradability restrict the use of quats ever more to ecologically insensitive fields of application, for example onshore.

EP-B-0 946 788 describes a process for protecting metal surfaces against corrosion using ester quats which, it is disclosed, have good biodegradability and low aquatic toxicity.

EP-A-0 320 769 discloses optionally quaternized fatty acid esters of oxyalkylated alkylamino alkylenamines and their use as corrosion inhibitors.

EP-B-0 212 265 describes quaternary polycondensates of alkoxylated alkylamines and dicarboxylic acids and their use as corrosion inhibitors and demulsifiers in crude oils.

EP-B-0 446 616 describes ampholytes and betaines based on fatty acid amido alkylamines which have very good corrosion protection and significantly reduced algae toxicity under the given test conditions.

EP-B-0 584 711 discloses esters, amides and imides of alkenylsuccinic acids with alkoxyalkylamines and their metal or ammonium salts as emulsifiers and corrosion inhibitors for metalworking assistants. The use of alkenylsuccinic esters or amido amine quats or corresponding betaines is not described.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is always stabilized by the incorporation of gas molecules. Depending on pressure and gas composition, these icelike compounds can exist even to above the freezing point of water (up to above 25° C.).

In the crude oil and natural gas industry, great significance attaches in particular to the gas hydrates which form from water and the natural gas constituents methane, ethane, propane, isobutane, n-butane, nitrogen, carbon dioxide and hydrogen sulfide. Especially in modem natural gas extraction, the existence of these gas hydrates constitutes a great problem, especially when wet gas or multiphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or multiphasic mixtures are transported over long distances, as occurs especially in colder regions of the earth or on the seabed.

In addition, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of multiphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore being made today to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or antiagglomerates). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or agglomeration inhibitors. Of particular significance in this context are polymers having a carbon backbone which contain both cyclic (pyrrolidone or caprolactam radicals) and acyclic amide structures in the side groups.

EP-B-0 736 130 discloses a process for inhibiting gas hydrates which entails feeding a substance of the formula

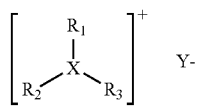

where X=S, N—R$_4$ or P—R$_4$, R$_1$, R$_2$ and R$_3$ =alkyl having at least 4 carbon atoms, R$_4$ =H or an organic radical, and Y=anion.

This therefore includes compounds of the formula

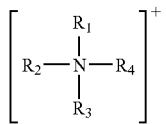

where R$_4$ may be any desired radical, but the R$_1$ to R$_3$ radicals have to be alkyl radicals having at least 4 carbon atoms.

EP-B-0 824 631 discloses a process for inhibiting gas hydrates which entails feeding a substance of the formula

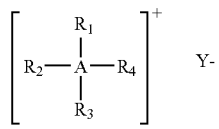

where R$_1$, R$_2$=linear/branched alkyl radicals having 4 or 5 carbon atoms, R$_3$, R$_4$=organic radicals having at least 8 carbon atoms and A=nitrogen or phosphorus. Y$^-$ is an anion. Two of the R$_1$ to R$_4$ radicals have to be linear or branched alkyl radicals having 4 or 5 carbon atoms.

U.S. Pat. No. 5,648,575 discloses a process for inhibiting gas hydrates. The process comprises the use of a compound of the formula

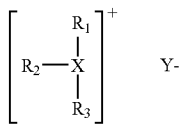

where R$^1$, R$^2$ are linear or branched alkyl groups having at least 4 carbon atoms, R$^3$ is an organic radical having at least 4 atoms, X is sulfur, NR$^4$ or PR$^4$, R$^4$ is hydrogen or an organic radical, and Y is an anion. The document discloses only those compounds which have at least two alkyl radicals having at least 4 carbon atoms.

U.S. Pat. No 6,025,302 discloses polyetheramine ammonium compounds as gas hydrate inhibitors whose ammonium nitrogen atom, in addition to the polyetheramine chain, bears 3 alkyl substituents.

WO-99/13197 discloses ammonium compounds as gas hydrate inhibitors which have at least one alkoxy group esterified with alkylcarboxylic acids. The advantages of using alkenylsuccinic acid derivatives are not disclosed.

WO-01/09082 discloses a process for preparing quaternary amines which, however, bear no alkoxy groups, and their use as gas hydrate inhibitors.

WO-00/078706 discloses quaternary ammonium compounds as gas hydrate inhibitors which, however, bear no carbonyl radicals.

EP-B-0 914 407 discloses the use of trisubstituted amine oxides as gas hydrate inhibitors.

U.S. Pat. No 5,254,138 discloses detergent additives for diesel fuel, said additives comprising polyamine derivatives of succinimide.

It is an object of the present invention to find novel corrosion inhibitors which, coupled with equally good or improved corrosion protection, offer not only optimum water solubility, more rapid film formation and therefore improved film persistence, but also improved biodegradability in comparison to the prior art corrosion inhibitors.

It is a further object of the present invention to find improved additives which not only slow the formation of gas hydrates (kinetic inhibitors) but also keep gas hydrate agglomerates small and pumpable (antiagglomerates), in order to thus ensure a broad spectrum of application with a high action potential. In addition, it should be possible to replace the thermodynamic inhibitors used currently (methanol and glycols) which cause considerable safety problems and logistical problems.

Prior art gas hydrate inhibitors are commonly coadditized with corrosion inhibitors, in order to prevent corrosion of the transport and extraction equipment. As a consequence of the frequent lack of immediate compatibility of gas hydrate inhibitor and corrosion protector in the course of formulation, there is additional work for the user. It would be a significant advantage over the prior art if coadditization with corrosion inhibitors were no longer obligatory.

It has now been found that, surprisingly, quaternary alkylaminoalkyl esters and quaternary alkylaminoalkyl amides, optionally containing quaternary alkylaminoalkyl imides, of alkenylsuccinic acids exhibit excellent action as corrosion inhibitors and gas hydrate inhibitors, and also improved film persistence and good biodegradability.

The present invention therefore provides the use of compounds of the formula (1)

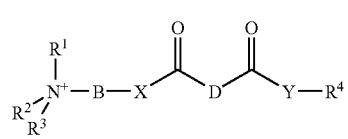

where
R$^1$, R$^2$ are each independently C$_1$- to C$_{22}$-alkyl, C$_2$- to C$_{22}$-alkenyl, C$_6$- to C$_{30}$-aryl or C$_7$- to C$_{30}$-alkylaryl,
R$^3$ is C$_1$- to C$_{22}$-alkyl, C$_2$- to C$_{22}$-alkenyl, C$_6$- to C$_{30}$-aryl or C$_7$- to C$_{30}$-alkylaryl, —CHR$^5$—COO$^-$ or —O$^-$,
R$^4$ is M, hydrogen or an organic radical which optionally contains heteroatoms and has from 1 to 100 carbon atoms,
B is an optionally substituted C$_1$- to C$_{10}$-alkylene group,
D is an ethylene group substituted by an organic radical having from 1 to 600 carbon atoms,
X, Y are each independently O or NR$^6$,
R$^5$, R$^6$ are each independently hydrogen, C$_1$- to C$_{22}$-alkyl, C$_2$- to C$_{22}$-alkenyl, C$_6$- to C$_{30}$-aryl or C$_7$- to C$_{30}$-alkylaryl, and
M is a cation as corrosion and gas hydrate inhibitors.

The invention further provides a method for inhibiting corrosion on metal surfaces, in particular ferrous surfaces, by adding at least one compound of the formula (1) to a corrosive system which is in contact with the metal surfaces.

The invention further provides a method for inhibiting gas hydrates by adding at least one compound of the formula (1) to a system of water and hydrocarbons which tends to the formation of gas hydrates.

The invention further provides the compounds of the formula (1).

For the purposes of this invention, corrosive systems are preferably liquid/liquid or liquid/gaseous multiphase systems consisting of water and hydrocarbons which comprise corrosive constituents, such as salts and acids, in free and/or dissolved form. The corrosive constituents may also be gaseous, for instance hydrogen sulfide and carbon dioxide.

For the purposes of this invention, hydrocarbons are organic compounds which are constituents of the crude oil/natural gas, and their secondary products. For the purposes of this invention, hydrocarbons are also volatile hydrocarbons, for example methane, ethane, propane, butane. For the purposes of this invention, they also include the further gaseous constituents of crude oil/natural gas, for instance hydrogen sulfide and carbon dioxide.

B may be straight-chain or branched and is preferably a $C_2$- to $C_4$-alkylene group, in particular an ethylene or propylene group. B may optionally be substituted by functional groups, preferably by one or more OH groups. $R^1$ and $R^2$ are preferably each independently an alkyl or alkenyl group of from 2 to 14 carbon atoms, in particular those groups having from 3 to 8 carbon atoms and especially butyl groups.

$R^3$ is preferably an alkyl or alkenyl group having from 1 to 12 carbon atoms, in particular having from 1 to 4 carbon atoms.

$R^5$ and $R^6$ are preferably each hydrogen. $R^4$ may be any desired organic radical which contains from 1 to 100 carbon atoms and which may optionally contain heteroatoms. When $R^4$ contains heteroatoms, they are preferably nitrogen or oxygen atoms or both, preferably both. The nitrogen atoms may be present in quaternized form.

$R^4$ is preferably a radical of the formula (2)

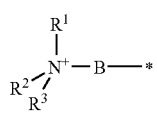

(2)

where $R^1$, $R^2$, $R^3$ and B are each as defined above with the areas of preference specified above in each case for $R^1$, $R^2$, $R^3$ and B.

In a further preferred embodiment, $R^4$ includes hydrogen which may be present either in covalently bound or dissociated form.

Together with the carbonyl groups to which it is bonded, D forms a substituted succinic acid derivative. D is therefore a structural unit of the formula

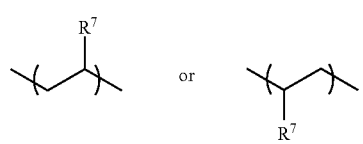

in which $R^7$ is any desired organic radical which optionally contains heteroatoms and has from 1 to 600 heteroatoms, and is in particular $C_2$- to $C_{100}$-alkyl or alkenyl radicals. The $R^7$ alkenyl radicals may be derived from $C_2$- to $C_8$-alkenes by oligomerization, in particular from ethylene, propylene or butylene.

When $R^7$ contains heteroatoms, they are preferably nitrogen or oxygen atoms or both, preferably both. The nitrogen atoms may be present in quaternized form.

$R^7$ preferably contains structural units of the formula (3)

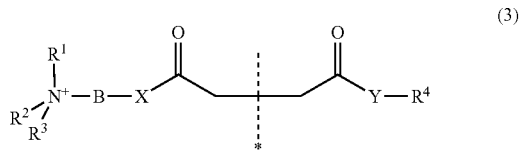

(3)

where $R^1$, $R^2$, $R^3$, $R^4$, B, X and Y are each as already defined above with the areas of preference specified above in each case for $R^1$, $R^2$, $R^3$, $R^4$, B, X and Y. The dotted line means that the structural units of the formula (3) may be bonded either in the 2- or the 3-position of the dicarbonyl group via a valence of an alkyl or alkenyl radical at any desired point on $R^7$. M is a mono- or polyvalent cation, preferably metal ion, more preferably alkali metal or alkaline earth metal ions.

In a further preferred embodiment, M is an ammonium ion of the formula $N^+R^8R^9R^{10}R^{11}$, where $R^8$, $R^9$, $R^{10}$ and $R^{11}$ are each independently hydrogen or any desired organic radical which contains from 1 to 100 carbon atoms, and which may optionally contain heteroatoms. When $R^8$, $R^9$, $R^{10}$ and/or $R^{11}$ contain heteroatoms, they are preferably nitrogen or oxygen atoms or both, preferably both. The nitrogen atoms may be present in quaternized form.

When $R^3$ is $C_1$- to $C_{22}$-alkyl, $C_2$- to $C_{22}$-alkenyl or $C_6$- to $C_{30}$-alkylaryl, suitable counterions for the compounds of formula (1) to (3) are any anions which do not impair the solubility of the compounds of the formula (1) to (3) in the organic-aqueous mixed phases. Such counterions are, for example, methylsulfate ions (methosulfate) or halide ions.

When $R^3$ is —$CHR^5$—$COO^-$ or —$O^-$, the compounds of the formula (1) to (3) are betaines and amine oxides respectively and, as internal salts (ampholytes), have an intramolecular counterion.

The compounds according to the invention can be used alone or in combination with other known corrosion inhibitors and/or gas hydrate inhibitors. In general, sufficient corrosion inhibitor and/or gas hydrate inhibitor according to the invention is used to obtain sufficient corrosion protection and protection from gas hydrate formation under the given conditions.

Preferred use concentrations of the corrosion inhibitors based on the pure compounds of the invention are from 5 to 5000 ppm, preferably from 10 to 1000 ppm, in particular from 15 to 150 ppm.

The gas hydrate inhibitors are generally used in amounts between 0.01 and 5% by weight of the pure compounds according to the invention based on the aqueous phase, preferably between 0.05 and 2% by weight.

Also particularly suitable as corrosion inhibitors and/or gas hydrate inhibitors are mixtures of the products according to the invention with other prior art corrosion inhibitors and/or gas hydrate inhibitors.

Particularly suitable corrosion inhibitors and therefore a preferred embodiment of this invention are mixtures of the compounds of the formula (1) to (3), such as amido amines and/or imidazolines of fatty acids and polyamines and their salts, quaternary ammonium salts, ethoxylated/propoxylated amines, amphoglycinates and -propionates, betaines or compounds described in DE-A-19 930 683.

Particularly suitable gas hydrate inhibitors and therefore a preferred embodiment of this invention are mixtures of the compounds of the formulae (1) to (3) with one or more polymers having a carbon backbone obtained by polymerization and amide bonds in the side chains. These include in particular homopolymers and/or copolymers of vinylpyrrolidone, vinylcaprolactam, isopropylacrylamide, acryloylpyrrolidine, N-methyl-N-vinylacetamide and also further anionic, cationic and neutral comonomers having a vinylic double bond.

When mixtures are used, the concentration ratios between the gas hydrate inhibitors according to the invention and the mixed-in components are from 90:10 to 10:90 percent by weight, and preference is given to mixtures in the ratios from 75:25 to 25:75, and in particular from 60:40 to 40:60.

The compounds according to the invention can be prepared by reacting substituted amino alcohols or substituted alkylenediamines with alkenylsuccinic acid derivatives to give the corresponding alkenylsuccinic mono- or diesters or mono- or diamides respectively, optionally to give cyclic alkenylsuccinimides, depending on the reaction ratios and reaction conditions. Subsequently, quaternization is effected using suitable alkylating agents.

The amino alcohols used are based on dialkylamines having $C_1$- to $C_{22}$-alkyl radicals or $C_2$- to $C_{22}$-alkenyl radicals, preferably $C_3$- to $C_8$-dialkylamines, which can be converted into the corresponding dialkylamino alcohols by prior art methods. Suitable dialkylamines are, for example, di-n-butylamine, diisobutylamine, dipentylamine, dihexylamine, dioctylamine, dicyclopentylamine, dicyclohexylamine, diphenylamine, dibenzylamine.

The alkylenediamines used are based substantially on dialkylaminoalkylenamines having $C_1$- to $C_{22}$-alkyl radicals or $C_2$- to $C_{22}$-alkenyl radicals, preferably tertiary $C_1$- to $C_8$-dialkylaminoalkylenamines. Particularly suitable are, for example, N,N-dibutylaminopropylamine, N,N-diethylaminopropylamine, N,N-dimethylaminopropylamine, N,N-dimethylaminobutylamine, N,N-dimethylaminohexylamine, N,N-dimethylaminodecylamine, N,N-dibutylaminoethylamine and N,N-dimethylamino-2-hydroxypropylamine.

The preparation of dialkylaminoalkylenamines is described in the prior art.

The alkenylsuccinic acid derivatives used are based on the free diacids, the diesters and the anhydrides. The alkenylsuccinic anhydrides are particularly suitable.

The preparation of alkenylsuccinic anhydrides by thermal or catalyzed "ene" reaction is described in the prior art. In this reaction, olefins, preferably olefins having a terminal double bond, are reacted with maleic anhydride under elevated temperatures. Depending on the reaction method, on the type of the olefin used and on the molar ratio used, mono- and/or bisadducts, in some cases polyadducts, are obtained.

The alkylsuccinic acid derivatives are generally reacted with the amino alcohols or alkylenedamines at 60-240° C., preferably at 120-200° C., in such a way that, in some cases depending on the alkenylsuccinic acid derivative used, there is complete condensation to the corresponding mono- or diesters, or mono- or dicarboxamides, in some cases to cyclic imides, with elimination of water of reaction or of alcohol. The degree of reaction can be followed by determination of the acid number, hydrolysis number and/or by the determination of the base and/or amide nitrogen.

The reaction proceeds without solvent, but can also preferably be carried out in solution. Especially when alkenylsuccinic acids are used, it is necessary to use solvents when high conversions and low acid numbers of the resulting reaction products are pursued. Suitable solvents for the preparation are organic compounds which azeotropically remove the water of reaction. In particular, aromatic solvents or solvent mixtures, or alcohols, can be used. Particular preference is given to 2-ethylhexanol. The reaction is then effected at the boiling point of the azeotrope.

When alkenylsuccinic diamides are prepared, preference is given to using alkenylsuccinic diester and an excess of the appropriate alkylenediamine, which can be distillatively removed with the alcohol being released or after the reaction. When alkenylsuccinic anhydrides are used, preference is given to iteratively fully esterifying with a suitable alcohol and then amidating. Suitable alcohols are, for example, ethanol, propanol, isopropanol or 2-ethylhexanol. Particular preference is given to 2-ethylhexanol.

When preparing the amides, the corresponding cyclic alkenylsuccinimides are inevitably by-produced, and are included.

According to the prior art, the esterifications and amidations can be accelerated by addition of suitable acid catalysts having a $PK_a$ of less than or equal to 5, for example mineral acids or sulfonic acids. Particular preference is given to alkylstannic acids.

For the preparation of the compounds according to the invention, the alkenylsuccinic mono- and diesters or mono- or diamides, optionally the alkenylsuccinic imides, are appropriately quaternized in a subsequent reaction step. The quaternization may be effected by appropriate alkylating agents at from 50 to 150° C. Suitable alkylating agents are alkyl halides and alkyl sulfates, preferably methyl chloride, methyl iodide, butyl bromide and dimethyl sulfate.

For the preparation of the betaines according to the invention, reaction is effected with a halocarboxylic acid and a base, preferably chloroacetic acid and sodium hydroxide. This may be effected by initially charging the alkylamino amides and/or alkylamino imides with from 50 to 125 mol % of halocarboxylic acid at 40° C. and reacting at from 40 to 100° C. by adding the base and the amount remaining up to 125 mol % of halocarboxylic acid, all at once or in portions. The basic compounds used may be alkali metal/alkaline earth metal hydroxides or alkoxides (sodium methoxide, sodium ethoxide, potassium tert-butoxide), but preferably alkali metal hydroxides, particularly sodium hydroxide or potassium hydroxide, in particular their aqueous solutions.

The amine oxides according to the invention are prepared by existing prior art processes, preferably by oxidation of the appropriate tertiary amine group with peroxides or peracids, preferably with hydrogen peroxide.

The reactions to give the quaternary alkenylsuccinic mono- or diesters or mono- or diamides, optionally to give cyclic alkenylsuccinic imides proceed without solvent, but can also preferably be carried out in solution. Suitable solvents for the preparation of quats, betaines and amine oxides are inert alcohols such as isopropanol, 2-ethylhexanol, or inert ethers such as tetrahydrofuran, glyme, diglyme and MPEGs.

Depending on the given requirements, the solvent used may remain in the product according to the invention or has to be removed distillatively.

EXAMPLES a) General Method for the Preparation of Alkylaminoalkyl Esters from Alkenylsuccinic Anhydrides A stirred apparatus equipped with a reflux condenser was initially charged with 0.3 mol of the appropriate alkenylsuccinic anhydride (based on hydrolysis number) with nitrogen purging and heated to 60° C. 0.3 mol of the appropriate amino alcohol was then added dropwise over 0.5 hour, in the course of which the reaction mixture is heated to approximately 70° C. The reaction mixture was stirred at 60° C. for a further 5 h.

Example 1

(N,N-Dibutylamino-N-ethyl tetrapropylenesuccinate) 87.8 g of tetrapropylenesuccinic anhydride (HN=383.3 mg KOH/g) and 52.0 g of dibutylaminoethanol (DBAE; OHN=323.8 mg KOH/g) were used to obtain 139 g of N,N-dibutylamino-N-ethyl tetrapropylenesuccinate having AN=133.4 mg KOH/g and basic N=2.93%.

Example 2

(N,N-Dibutylamino-N-ethyl pentapropylenesuccinate) 117.4 g of pentapropylenesuccinic anhydride (HN=286.7 mg KOH/g) and 52.0 g of dibutylaminoethanol (DBAE; OHN=323.8 mg KOH/g) were used to obtain 169 g of N,N-dibutylamino-N-ethyl pentapropylenesuccinate having AN=118.7 mg KOH/g and basic N=2.45%.

Example 3

(N,N-Dibutylamino-N-ethyl polyisobutenylsuccinate) 130.5 g of polyisobutenylsuccinic anhydride (based on PIB 550; HN=257.9 mg KOH/g) and 52.0 g of dibutylaminoethanol (DBAE; OHN=323.8 mg KOH/g) were used to prepare 182 g of N,N-dibutylamino-N-ethyl polyisobutenylsuccinate having AN=106.1 mg KOH/g and basic N=2.27%.

b) General Method for the Preparation of the Alkylaminoalkyl Diesters from Dicarboxylic Anhydrides A stirred apparatus equipped with distillation head with condenser was initially charged with 0.3 mol of the appropriate alkenylsuccinic anhydride (based on hydrolysis number) with nitrogen purging and heated to 60° C. 0.6 mol of the appropriate amino alcohol was then added dropwise over 0.5 hour, in the course of which the reaction mixture is heated to approx. 70° C. The reaction mixture was then stirred at 60° C. for a further 0.5 h and then heated to 180° C., and water of reaction was distilled off at this temperature for 5 h. Finally, the water of reaction was removed at 200° C. and 200 mbar for 2 h until acid number (AN) of less than 10 mg KOH/g had been attained.

Example 4

(bis[(N,N-Dibutylamino-N-ethyl]tetrapropylenesuccinate) 87.8 g of tetrapropylenesuccinic anhydride (HN=383.3 mg KOH/g) and 104.0 g of dibutylaminoethanol (DBAE; OHN=323.8 mg KOH/g) were used to obtain 172 g of bis[N,N-dibutylamino-N-ethyl]tetrapropylenesuccinate having AN=7.1 mg KOH/g, HN=142.4 mg KOH/g and basic N=4.34%.

Example 5

(bis[(N,N-Dibutylamino-N-ethyl]pentapropylenesuccinate) 117.4 g of pentapropylenesuccinic anhydride (HN=286.7 mg KOH/g) and 104.0 g of dibutylaminoethanol (DBAE; OHN=323.8 mg KOH/g) were used to obtain 205 g of bis[N,N-dibutylamino-N-ethyl]pentapropylenesuccinate having AN=9.6 mg, HN=100.3 mg KOH/g and basic N=4.62%.

Example 6

(bis[(N,N-Dibutylamino-N-ethyl]polyisobutenylsuccinate) 130.5 g of polyisobutenylsuccinic anhydride (based on PIB 550; HN=257.9 mg KOH/g) and 104.0 g of dibutylaminoethanol (DBAE; OHN=323.8 mg KOH/g) were used to prepare 200 g of bis[N,N-dibutylamino-N-ethyl]polyisobutenylsuccinate having AN=6.6 mg KOH/g, HN=117.5 mg KOH/g and basic N=4.40%.

c) General Method for the Quaternization with Dimethyl Sulfate

A stirred apparatus was initially charged with 0.2 mol (based on basic N) of the appropriate amine with nitrogen purging and heated to 60° C. 0.19 mol of dimethyl sulfate was added dropwise thereto in such a way that the reaction temperature did not exceed 80-90° C. The reaction mixture was subsequently stirred at 90° C. for a further 3 h. This method was used to quaternize the compounds described by examples 1 to 6 (examples 7 to 12, as listed in tables 1 and 2).

Effectiveness of the compounds according to the invention as corrosion inhibitors.

The compounds according to the invention were tested as corrosion inhibitors in the Shell wheel test. Coupons of carbon steel (DIN 1.1203 having 15 cm$^2$ surface area) were immersed in a salt water/petroleum mixture (9:1.5% NaCl solution, adjusted to pH 3.5 using acetic acid) and subjected to this medium at a rotation rate of 40 rpm at 70° C. for 24 hours. The dosage of the inhibitor was 50 ppm of a 40% solution of the inhibitor. The protection values were calculated from the mass reduction of the coupons, based on a blank value.

In the table follows, "comparison 1" refers to a commercial residue amine, quat based on dicocoalkyldimethylammonium chloride and "comparison 2" to a commercial soya fatty acid amidopropyl-N,N-dimethylammonium carboxymethyl betaine described by EP-B-0 446 616 (prior art corrosion inhibitors).

TABLE 1

(SHELL wheel test)

| Example | Corrosion inhibitor | Ø Protection % |
|---|---|---|
| Comparison 1 | Standard quat | 36.0 |
| Comparison 2 | Standard betaine | 75.4 |
| 7 | Quat from example 1 | 87.6 |
| 8 | Quat from example 2 | 90.1 |
| 9 | Quat from example 3 | 92.4 |
| 10 | Quat from example 4 | 70.5 |
| 11 | Quat from example 5 | 84.1 |
| 12 | Quat from example 6 | 89.3 |

The products were also tested in the LPR test (test conditions similar to ASTM D 2776).

TABLE 2

(LPR test)

| Example | Corrosion inhibitor | Protection after [%] | | |
|---|---|---|---|---|
| | | 10 min | 30 min | 60 min |
| Comparison 1 | Standard quat | 53.9 | 61.2 | 73.7 |
| Comparison 2 | Standard betaine | 45.9 | 59.2 | 64.3 |
| 7 | Quat from example 1 | 58.8 | 74.5 | 81.0 |
| 8 | Quat from example 2 | 50.3 | 72.1 | 84.8 |
| 9 | Quat from example 3 | 52.1 | 73.6 | 85.0 |
| 10 | Quat from example 4 | 84.1 | 89.7 | 91.7 |
| 11 | Quat from example 5 | 86.5 | 90.7 | 91.6 |
| 12 | Quat from example 6 | 86.3 | 91.0 | 91.7 |

As can be seen from the above test results, the products according to the invention have very good corrosion protection properties at low dosage and substantially exceed the effectiveness of the prior art inhibitors. As a consequence of their ester and amide structure, the compounds have better biodegradability and can be used at a lower dosage.

What is claimed is:

1. A compound of formula (1)

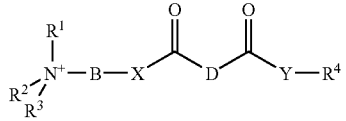

where $R^1$, $R^2$ are each independently $C_1$- to $C_{22}$-alkyl, $C_2$- to $C_{22}$-alkenyl, $C_6$- to $C_{30}$-aryl or $C_7$- to $C_{30}$-alkylaryl, $R^3$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$, $R^4$ is M, hydrogen or an organic radical having from 1 to 100 carbon atoms, B is a straight-chain or branched $C_1$- to $C_{10}$-alkylene group, D is an ethylene group substituted by an organic radical having from 1 to 600 carbon atoms, X, Y are each independently O or $NR^6$, $R^5$, $R^6$ are each independently hydrogen, $C_1$- to $C_{22}$-alkyl, $C_2$- to $C_{22}$-alkenyl, $C_6$- to $C_{30}$-aryl or $C_7$- to $C_{30}$-alkylaryl, and M is a cation.

2. The compound of claim 1, wherein $R^4$ contains hetero atoms.

* * * * *